(12) United States Patent
Hamilton et al.

(10) Patent No.: US 11,925,486 B2
(45) Date of Patent: Mar. 12, 2024

(54) APPARATUS AND METHOD FOR OPERATING A MEDICAL IMAGING DEVICE

(71) Applicant: Siemens Healthcare GmbH, Erlangen (DE)

(72) Inventors: Kathrin Friederike Hamilton, Hallstadt (DE); Hans-Jürgen Müller, Pretzfeld (DE); Sebastian Schneider, Schaafheim (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 72 days.

(21) Appl. No.: 17/704,487

(22) Filed: Mar. 25, 2022

(65) Prior Publication Data
US 2022/0313175 A1 Oct. 6, 2022

(30) Foreign Application Priority Data
Mar. 30, 2021 (EP) .................................... 21166034

(51) Int. Cl.
*A61B 5/00* (2006.01)

(52) U.S. Cl.
CPC .......... *A61B 5/7455* (2013.01); *A61B 5/0033* (2013.01); *A61B 2560/0475* (2013.01); *A61B 2560/0487* (2013.01); *A61B 2560/06* (2013.01)

(58) Field of Classification Search
CPC ................ A61B 5/7455; A61B 5/0033; A61B 2560/0475; A61B 2560/0487; A61B 2560/06; A61B 6/46; A61B 6/467; A61B 6/037; G06F 3/04847; G06F 2203/014; G06F 3/0488; G06F 3/016
See application file for complete search history.

(56) References Cited

U.S. PATENT DOCUMENTS

| | | | |
|---|---|---|---|
| 10,926,136 B1* | 2/2021 | Mogford | A61B 5/1107 |
| 2011/0032091 A1 | 2/2011 | Park et al. | |
| 2015/0145783 A1 | 5/2015 | Redelsheimer et al. | |
| 2016/0266760 A1 | 9/2016 | Beckmann et al. | |
| 2019/0339776 A1 | 11/2019 | Rosenberg et al. | |
| 2020/0029936 A1* | 1/2020 | Sato | B06B 1/0622 |
| 2021/0030497 A1* | 2/2021 | Daley | A61B 90/361 |
| 2021/0177270 A1* | 6/2021 | Sankai | G01N 29/30 |
| 2022/0314274 A1* | 10/2022 | Meynier | B06B 1/0292 |

FOREIGN PATENT DOCUMENTS

EP 2876527 A1 5/2015

* cited by examiner

*Primary Examiner* — Ojiako K Nwugo
(74) *Attorney, Agent, or Firm* — Harness, Dickey & Pierce, P.L.C.

(57) ABSTRACT

The apparatus has a control unit, a connection unit and a vibration unit. The connection unit has a control-element-side region, an edge region and a flexible region, wherein the control-element-side region is flexibly mounted relative to the edge region by the flexible region. The control unit has a contact region, wherein the contact region is fixed relative to the control-element-side region. The control unit is configured to generate a contact signal based on contact with the contact region. The vibration unit is configured to induce a vibration of the contact region relative to the edge region during contact with the contact region.

20 Claims, 8 Drawing Sheets

APPARATUS AND METHOD FOR OPERATING A MEDICAL IMAGING DEVICE

CROSS-REFERENCE TO RELATED APPLICATION(S)

The present application hereby claims priority under 35 U.S.C. § 119 to European Patent Application No. EP 21166034.5, filed Mar. 30, 2021, the entire contents of which are hereby incorporated herein by reference.

FIELD

Embodiments of the present invention relate to an apparatus for operating a medical imaging device, a medical imaging device and/or a method for operating a medical imaging device.

BACKGROUND

A multiplicity of different problems can arise during operation of a medical imaging device, for example a computed tomography device, via a control unit, for example in the form of a human-machine interface (HMI for short). In particular, these problems relate to the safety of the medical imaging device and of the user, as well as to ergonomics.

SUMMARY

In accordance with a basic sequence of a human-machine interaction it is provided that the machine signals the various control options to the user; the user selects and activates a function, in particular via an input; the machine registers and processes the input; the machine activates the desired function; the machine generates feedback for the user; and the user registers and interprets the feedback. Misunderstandings or erroneous interpretations within this interaction sequence can arise at various points, as a result of which the entire interaction can be negatively impacted.

Human-machine interfaces on medical imaging devices can for example provide visual, acoustic and/or haptic feedback for the user.

Visual feedback can be provided for example via an illuminated scale and/or via a display. Acoustic feedback can be provided for example via a signal generator and/or via a loudspeaker. Haptic feedback can be provided for example via a movable operating element, via a tangible surface property and/or via a pushbutton as an operating element.

Feedback generated by the human-machine interface can be attuned in particular to a specific sensory organ of the user. Since this sensory organ cannot always be attained, successful feedback may therefore fail to materialize. For example, visual feedback is recognized only if the user looks at the corresponding display. To increase the chances of successful feedback, the feedback can be provided on multiple different channels, in particular can be provided redundantly. For example, it can be provided that via a control unit both visual feedback and acoustic feedback is provided, in particular is provided in parallel in time.

The user can feel movable operating elements during operation and can thus detect haptic feedback. Capacitive control elements can be used in order to generate good hygiene conditions and to prevent interstices from arising in the surface of the casing of the medical imaging device. Said capacitive control elements can in particular be designed with a smooth surface, in order for example to enable contact with the smooth surface in the form of a swiping motion. The smooth surface of the capacitive control element can of course be configured to be visually readily identifiable, but during operation there is no movable operating element that can be sensed in order to provide the user with haptic feedback about the success of his or her input. This can have various undesired consequences, for example that in addition to the user's hand, which performs the contact, at least one further sensory organ of the user has to be used for the operation of the medical imaging device in order to obtain feedback, for example visually and/or acoustically. As a result there may be an increased risk that successful feedback will fail to materialize.

At least one object of embodiments of the present invention is to provide an apparatus for operating a medical imaging device which represents an improvement in respect of feedback to the user.

An embodiment of the present invention relates to an apparatus for operating a medical imaging device,
wherein the apparatus has a control unit, a connection unit and a vibration unit,
wherein the connection unit has a control-element-side region, an edge region and a flexible region, wherein the control-element-side region is flexibly mounted relative to the edge region via the flexible region,
wherein the control unit has a contact region, wherein the contact region is fixed relative to the control-element-side region,
wherein the control unit is designed to generate a contact signal on the basis of contact with the contact region,
wherein the vibration unit is designed to induce a vibration of the contact region relative to the edge region during contact with the contact region, in particular to induce it such that the vibration comprises tactile feedback in respect of contact with the contact region, in particular comprises it such that the tactile feedback can be detected via contact with the contact region.

In particular it can be provided that the vibration unit is designed to induce a vibration of the control-element-side region relative to the edge region during contact with the contact region, wherein the vibration of the control-element-side region relative to the edge region during contact with the contact region brings about the vibration of the contact region relative to the edge region during contact with the contact region, in particular brings it about in that the contact region is fixed relative to the control-element-side region.

To make it possible to feel for a position of the contact region, the contact region and/or the control-element-side region can have a haptically detectable surface structure.

In particular it can be provided that the vibration unit has at least one vibration motor to induce the vibration.

Examples of vibration motors that can be used include motors with an eccentric rotating mass (ERM motor for short) and/or linear resonant actuators (LRA for short).

The vibration motors can in particular be embodied in the form of a disk and/or as a micro-vibration motor. In particular, vibration motors can be used, these being known to the person skilled in the art for example by the names coin vibration motor, pager vibration motor or pancake vibration motor.

Furthermore, it can be provided that the vibration unit has for example at least one acoustic signal generator and/or at least one piezo-actuator for inducing the vibration.

One form of embodiment provides that the control unit is further designed to send the contact signal to a data processing unit, wherein the data processing unit is designed to receive the contact signal, to generate a vibration signal on the basis of the contact signal and to send the vibration signal to the vibration unit, wherein the vibration unit is further designed to receive the vibration signal and to induce the vibration of the contact region relative to the edge region on the basis of the vibration signal.

One form of embodiment provides that the apparatus further has the data processing unit.

One form of embodiment provides that contact with the contact region relates to, in particular brings about, an input of a value for the operation of the medical imaging device, wherein the vibration of the contact region relative to the edge region during contact with the contact region comprises tactile feedback which relates to the value for the operation of the medical imaging device.

One form of embodiment provides that the vibration of the contact region relative to the edge region during contact with the contact region forms a carrier signal, wherein the carrier signal is modulated with a useful signal which relates to the value for the operation of the medical imaging device.

Furthermore, it can be provided that one parameter of the vibration is a function of the value for the operation of the medical imaging device, in particular is a monotonic function.

The parameter of the vibration can for example be selected from the group of vibration parameters which consists of a duration of the vibration, an amplitude of the vibration, a frequency of the vibration and combinations thereof.

Furthermore, it can be provided that the value for the operation of the medical imaging device is a function of a parameter of contact with the contact region, in particular is a monotonic function. The parameter of contact with the contact region can for example be a parameter of a swiping motion of contact with the contact region. The parameter of contact with the contact region can for example be selected from the group of contact parameters which consists of a duration of contact, an intensity of contact, a speed of the swiping motion of contact, a path of the swiping motion of contact, a distance covered by the swiping motion and combinations thereof.

For example, in the case of a capacitive slide control which does not have a movable operating element, an increasing vibration strength can give feedback about the switch position. Thus for example a change in position of a movable operating element of a slide control can be imitated.

Contact with the contact region can for example comprise a swiping motion along the contact region. In particular it can be provided that a plurality of positions of a finger and/or of a pointer, which is used for contact with the contact region, relative to the contact region are provided along the path of the swiping motion. In particular each position of the plurality of positions can be assigned a corresponding value for the operation of the medical imaging device. The vibration of the contact region relative to the edge region can for example comprise tactile feedback as to the position of the plurality of positions at which the finger and/or a pointer is located.

Furthermore, it can be provided that the vibration unit has a set of vibration motors, wherein the vibration motors in the set of vibration motors are arranged relative to one another, such that a reference plane runs through each vibration motor in the set of vibration motors.

In particular it can be provided that the vibration motors in the set of vibration motors are arranged about a reference axis perpendicular to the reference plane, such that the set of vibration motors has a corresponding vibration motor for any half-line that emanates from the reference axis and lies in the reference plane, so that an angular distance in relation to the reference axis between this half-line and the corresponding vibration motor, in particular between this half-line and the motor axis of the corresponding vibration motor, is not greater than 60 degrees, in particular not greater than 45 degrees, for example not greater than 30 degrees.

In particular it can be provided that the reference axis runs through a central region of the control-element-side region and/or that the control-element-side region extends in a planar fashion substantially parallel to the reference plane.

In particular it can be provided that a distance between the reference axis and the contact region is less than a distance between the reference axis and the vibration motor in the set of vibration motors which is closest to the reference axis.

In particular it can be provided that for each vibration motor in the set of vibration motors a motor axis of this vibration motor lies in the reference plane.

The motor axis can for example be an axis of rotation of a motor with an eccentric rotating mass, about which the eccentric mass rotates. The motor axis can for example be a linear axis of a linear resonant actuator.

Furthermore, it can be provided that the vibration unit has at least one further vibration motor, wherein the at least one further vibration motor is not contained in the set of vibration motors.

Furthermore, it can be provided that the connection unit has a flexible sealing ring, wherein a first annular contact surface of the flexible sealing ring is fixed relative to the control-element-side region. In particular it can be provided that a second annular contact surface of the flexible sealing ring forms at least one subregion of the edge region. In particular it can be provided that an annular subregion of the flexible sealing ring forms at least one subregion of the flexible region.

The annular subregion of the flexible sealing ring, which forms the at least one subregion of the flexible region, can in particular be located between the first annular contact surface of the flexible sealing ring and the second annular contact surface of the flexible sealing ring.

Embodiments of the present invention further relate to a medical imaging device, having the inventive apparatus and a casing for delimiting an internal region of the medical imaging device from a surrounding area, wherein the surrounding area surrounds the medical imaging device, wherein the edge region is fixed on the casing relative to the casing, in particular fixed such that the control-element-side region is flexibly mounted relative to the casing via the flexible region.

One form of embodiment provides that the casing has a recess, in which at least one part of the apparatus can be accommodated, wherein the at least one part of the apparatus is accommodated in the recess, wherein the edge region is attached to the casing in a form-fit manner and/or in a manner that is impervious to liquids along at least one annular contour that surrounds the recess.

Embodiments of the present invention further relate to a method for operating a medical imaging device via an apparatus, wherein the apparatus has a control unit, a connection unit and a vibration unit, wherein the connection unit has a control-element-side region, an edge region and a flexible region, wherein the control-element-side region is flexibly mounted relative to the edge region via the flexible region, wherein the control unit has a contact region, wherein the contact region is fixed relative to the control-element-side region, wherein a contact signal is generated via the control unit on the basis of contact with the contact region, wherein a vibration of the contact region relative to the edge region is induced during contact with the contact region via the vibration unit, in particular is induced such that the vibration comprises tactile feedback in respect of contact with the contact region, in particular such that the tactile feedback is detected via contact with the contact region.

In particular it can be provided that the vibration of the contact region relative to the edge region is induced during contact with the contact region via the vibration unit, in that a vibration of the control-element-side region relative to the edge region is induced via the vibration unit during contact with the contact region and thanks to the vibration of the control-element-side region relative to the edge region during contact with the contact region the vibration of the contact region relative to the edge region is brought about during contact with the contact region, in particular is brought about because the contact region is fixed relative to the control-element-side region.

In particular the medical imaging device can be operated in that thanks to contact with the contact region an input of a value for the operation of the medical imaging device can be brought about.

One form of embodiment provides that via the control unit the contact signal is sent to a data processing unit, wherein via the data processing unit the contact signal is received, a vibration signal is generated on the basis of the contact signal and the vibration signal is sent to the vibration unit, wherein the vibration signal is received via the vibration unit and the vibration of the contact region relative to the edge region is induced on the basis of the vibration signal.

One form of embodiment provides that contact with the contact region relates to, in particular brings about, an input of a value for the operation of the medical imaging device, wherein the vibration of the contact region relative to the edge region during contact with the contact region comprises tactile feedback, which relates to the value for the operation of the medical imaging device.

One form of embodiment provides that the vibration of the contact region relative to the edge region during contact with the contact region forms a carrier signal, wherein the carrier signal is modulated with a useful signal, which relates to the value for the operation of the medical imaging device.

One form of embodiment provides that one parameter of the vibration is a monotonic function of the value for the operation of the medical imaging device.

Furthermore, it can be provided that the apparatus can for example, in addition to the tactile feedback, provide visual, acoustic and/or haptic feedback, which in particular can relate to the value for the operation of the medical imaging device. Illuminated scales, displays, sound generators and/or a surface structure of the contact region that is changed in particular regions can for example be used for this purpose. By combining these different types of feedback the operating ergonomics and operating safety are additionally improved.

A successfully registered operation of the medical imaging device can thus be signaled to the user in a number of ways. An unsuccessful operation can be signaled to the user by the absence of any feedback. The contact can for example be performed by a user who is located in the surrounding area. Potential users are for example medical-technical personnel, radiologists and/or service employees.

The more unambiguously successful inputs on the one hand and unsuccessful inputs on the other hand that are signaled to the user, the lower the probability that the user will repeat the operation of the element in order to ensure an activation. A repeat operation can result in negative consequences, which can adversely affect user and system. If the system requires a certain time for a system response, it is possible that the user discerns this time not as waiting time, but as an unsuccessful input. As a result it is possible that the user makes a repeat input, which interferes with the previous input in an unpredictable way. Because the vibration of the contact region relative to the edge region is induced during contact with the contact region, it is possible to signal to the user during contact whether the input is successful or unsuccessful, so that unnecessary repeat inputs can be avoided.

Because optimum operability for the user is enabled, operating procedures can be carried out more smoothly and effectively. The increase in operating accuracy and operating safety means the number of erroneous operations, which could result in damage to people or equipment, can be reduced.

The medical imaging device can for example be selected from the group of imaging modalities which consists of an X-ray device, a C-arm X-ray device, a computed tomography device (CT device), a scintigraphy device, a single photon computed tomography device (SPECT device), a positron emission tomography device (PET device), a magnetic resonance tomography device (MR device) and combinations thereof, in particular a SPECT-CT device. The medical imaging device can further have a combination of an imaging modality, which is selected for example from the group of imaging modalities, and an irradiation modality. In this case the irradiation modality can for example have an irradiation unit for therapeutic irradiation.

The medical imaging device can for example have a gantry with a tunnel-shaped opening. In particular a patient can be introduced into the tunnel-shaped opening, in order to be examined by the medical imaging device.

The medical imaging device can in particular have the data processing unit. In particular it can be provided that the data processing unit is connected to the apparatus via a data transfer connection, in particular via a bidirectional data transfer connection and/or that the data processing unit is connected to the apparatus by electrical cables for the transmission of current and/or voltage. The data processing unit can for example be located inside the internal region and/or outside the gantry, in particular in an arithmetic unit separate from the gantry.

In connection with embodiments of the present invention, features which are described in respect of different forms of embodiments of the present invention and/or different claim categories (method, use, apparatus, system, arrangement, etc.) can be combined to form further forms of embodiments of the present invention. For example, a claim that relates to an apparatus can also be developed with features that are described or claimed in connection with a method, and vice versa. Functional features of a method can in this case be executed by correspondingly embodied aforementioned components.

BRIEF DESCRIPTION OF THE DRAWINGS

The present invention is explained in greater detail below using example embodiments with reference to the attached figures. The representation in the figures is schematic, greatly simplified and not necessarily true to scale.

DETAILED DESCRIPTION

Figure 1:
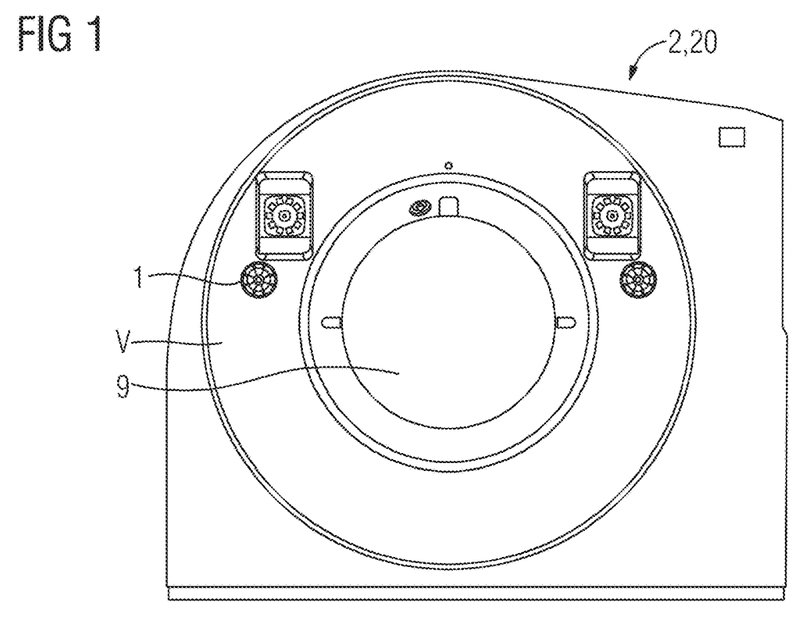
FIG. 1 shows a medical imaging device with an apparatus for operating the medical imaging device according to embodiments of the present invention.

FIG. 1 shows a medical imaging device 2 with an apparatus 1 for operating the medical imaging device 2 and a casing V for delimiting an internal region 4 of the medical imaging device 1 from a surrounding area 5, wherein the surrounding area 5 surrounds the medical imaging device 1.

The medical imaging device 2 has a gantry 20 with a tunnel-shaped opening 9. In particular, a patient can be introduced into the tunnel-shaped opening 9, in order to be examined by the medical imaging device 2.

Figure 2:
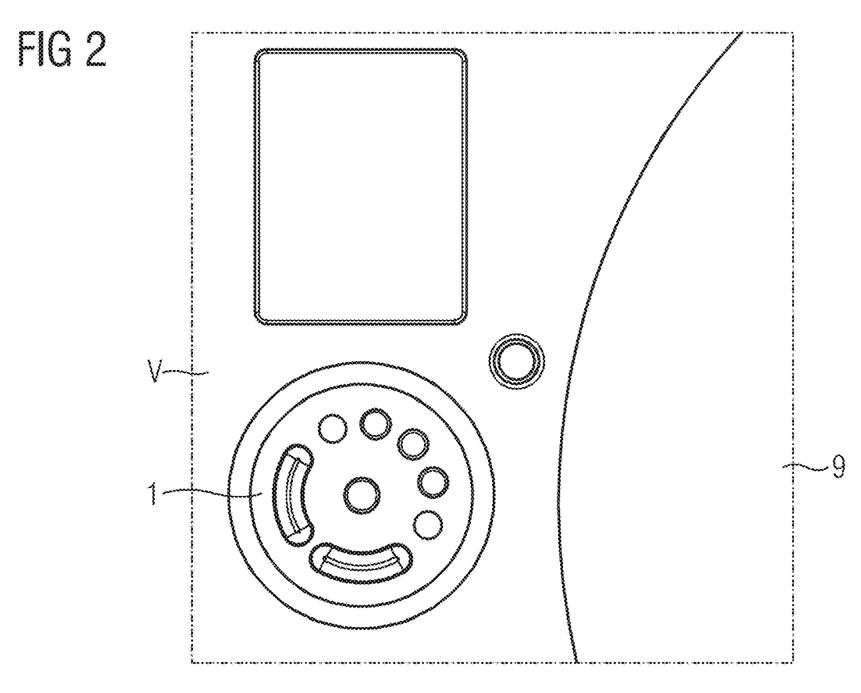
FIG. 2 shows a region of the casing of the medical imaging device with the apparatus for operating the medical imaging device according to embodiments of the present invention.

FIG. 2 shows a region of the casing V of the medical imaging device 2 with the apparatus 1 for operating the medical imaging device 2.

Figure 3:
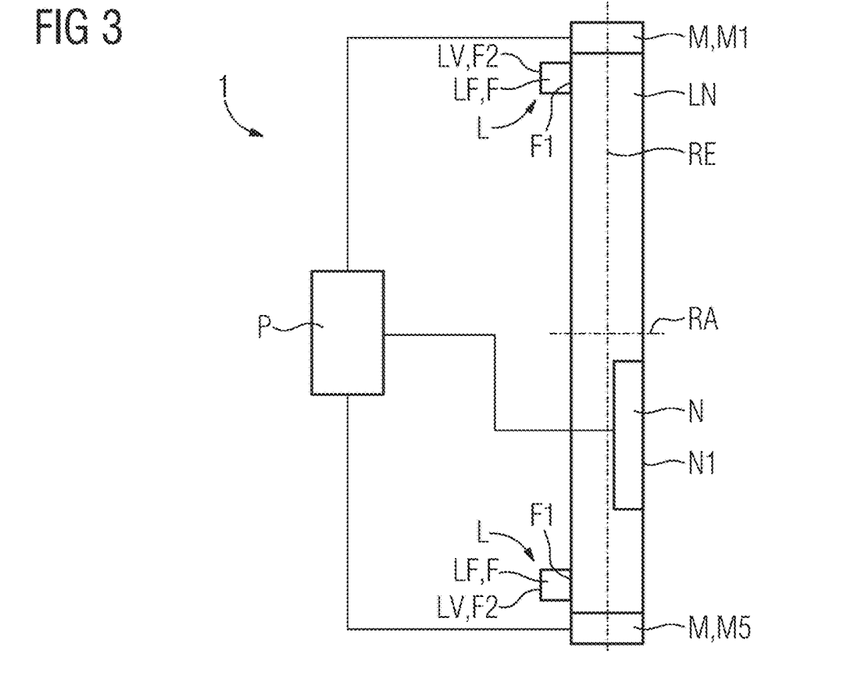
FIG. 3 shows a simplified representation of the apparatus for operating the medical imaging device according to embodiments of the present invention.

FIG. 3 shows a simplified sectional representation of the apparatus 1 for operating the medical imaging device 2. The apparatus 1 has a control unit N, a connection unit L and a vibration unit M. The connection unit L has a control-element-side region LN, an edge region LV and a flexible region LF, wherein the control-element-side region LN is flexibly mounted relative to the edge region LV via the flexible region LF, wherein the control unit N has a contact region N1, wherein the contact region N1 is fixed relative to the control-element-side region LN, wherein the control unit N is designed to generate S1 a contact signal on the basis of contact with the contact region N1.

The vibration unit M is designed to induce S2 a vibration of the contact region N1 relative to the edge region LV during contact with the contact region N1, in particular to induce it such that the vibration comprises tactile feedback in respect of contact with the contact region N1, in particular such that the tactile feedback can be detected via contact with the contact region N1.

The apparatus 1 further has the data processing unit P. The control unit N is further designed to send S11 the contact signal to a data processing unit P, wherein the data processing unit P is designed to receive SP0 the contact signal, to generate SP a vibration signal on the basis of the contact signal and to send SP1 the vibration signal to the vibration unit M, wherein the vibration unit M is further designed to receive S20 the vibration signal and to induce S2 the vibration of the contact region N1 relative to the edge region LV on the basis of the vibration signal.

Figure 4:
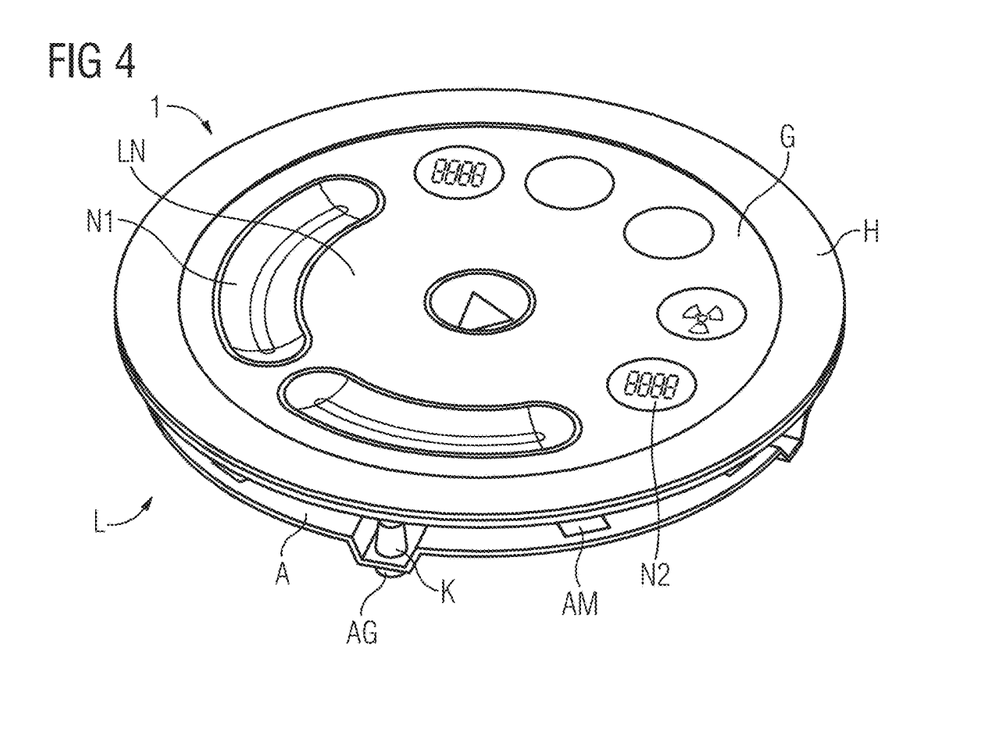
FIG. 4 shows the apparatus for operating the medical imaging device in a first view, according to embodiments of the present invention.

FIG. 4 shows the apparatus 1 for operating the medical imaging device 2 in a first view. The contact with the contact region N1 relates to, in particular brings about, an input of a value for the operation of the medical imaging device 2, wherein the vibration of the contact region N1 relative to the edge region LV during contact with the contact region N1 comprises tactile feedback, which relates to the value for the operation of the medical imaging device 2.

Figure 5:
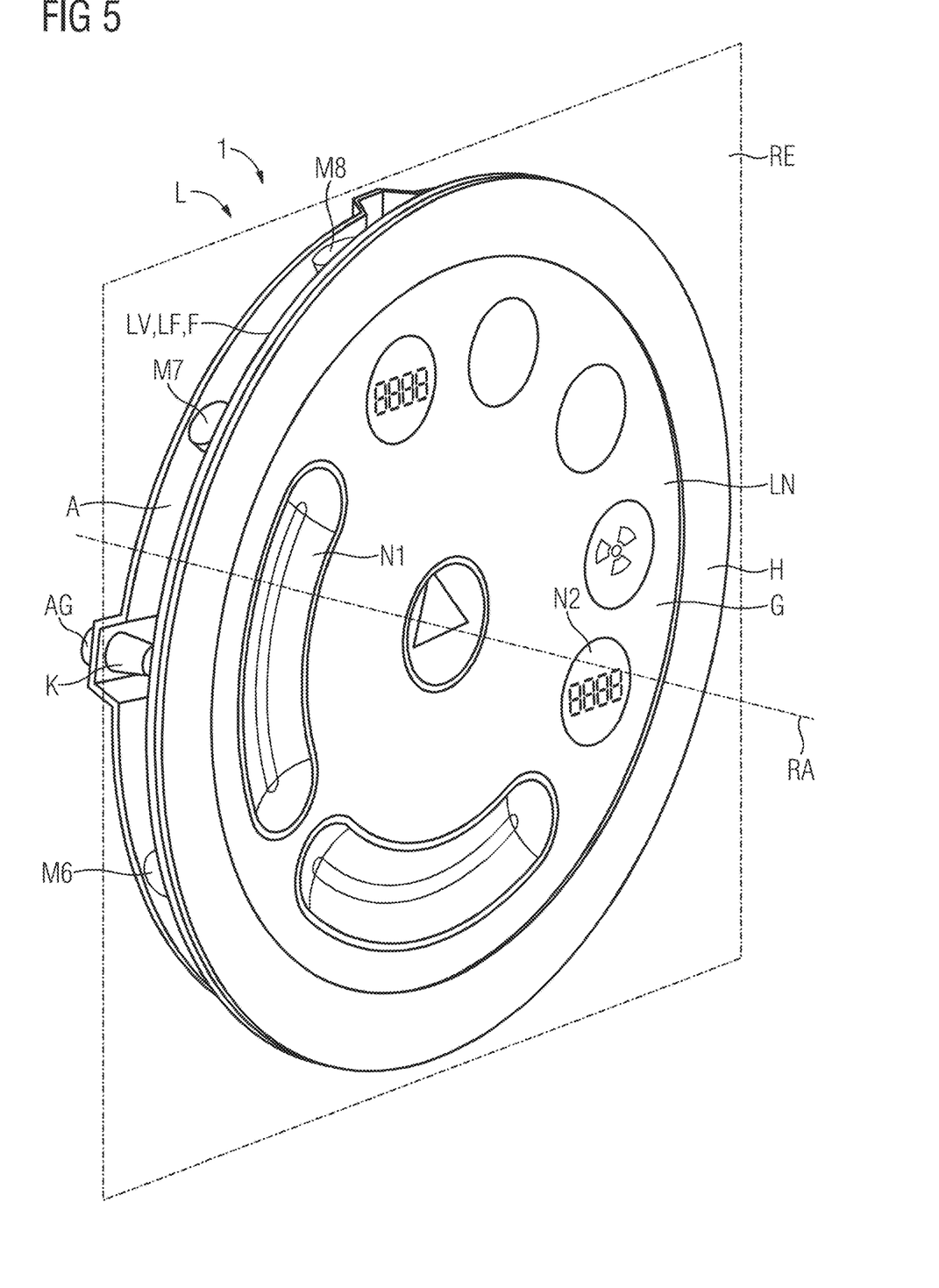
FIG. 5 shows the apparatus for operating the medical imaging device in a second view, according to embodiments of the present invention.

FIG. 5 shows the apparatus 1 for operating the medical imaging device 2 in a second view. The reference axis RA runs through a central region of the control-element-side region LN. The control-element-side region LN extends in a planar manner substantially in parallel to the reference plane RE.

Figure 6:
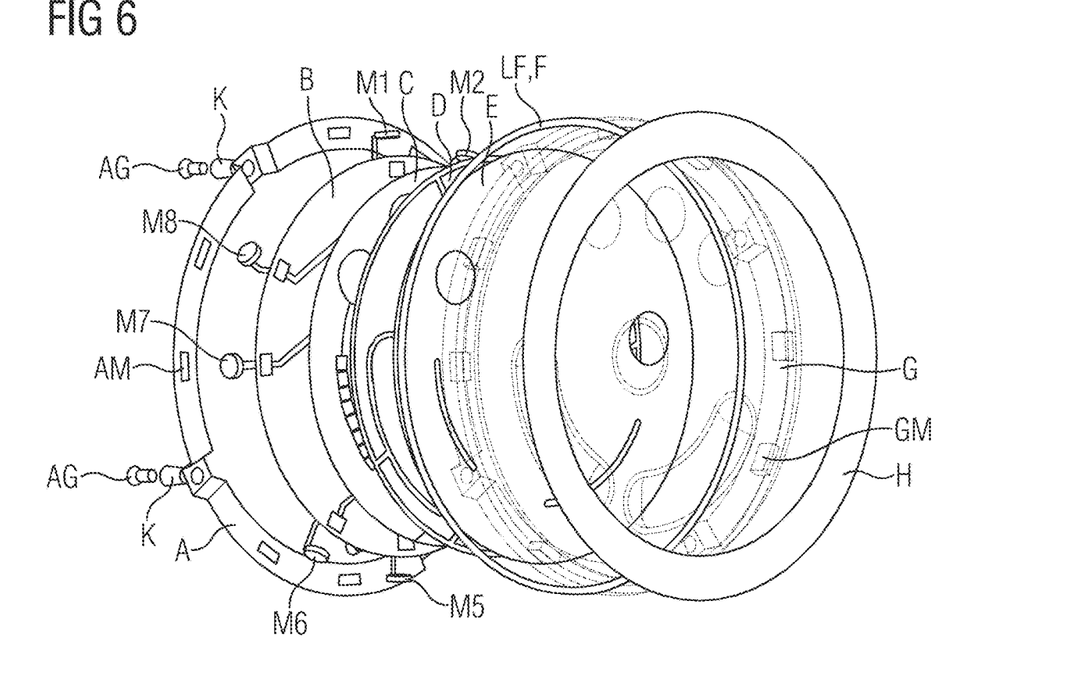
FIG. 6 shows an arrangement of components of the apparatus for operating the medical imaging device according to embodiments of the present invention.

FIG. 6 shows an arrangement of components of the apparatus 1 for operating the medical imaging device 2.

The housing G has a set of recesses GM. For each vibration motor in the set of vibration motors M1-M8 one recess in the set of recesses GM is provided, in which this vibration motor can be accommodated in a form-fit manner. In addition, the vibration motor accommodated in the recess can be bonded to the housing G.

The mounting ring A has a set of openings AM. For each vibration motor in the set of vibration motors M1-M8 one opening in the set of openings AM is provided, through which this vibration motor can be inserted, in order to be accommodated in the corresponding recess, if the mounting ring A is connected to the housing G.

Figure 7:
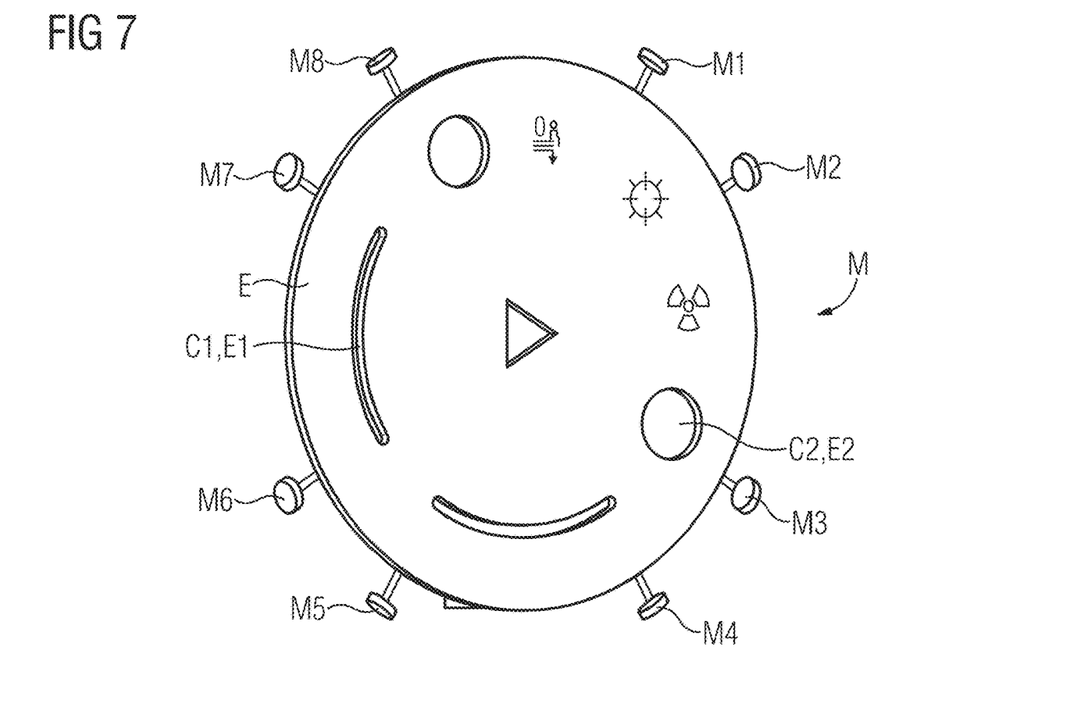
FIG. 7 shows a part of the apparatus for operating the medical imaging device according to embodiments of the present invention.

FIG. 7 shows a part of the apparatus 1 for operating the medical imaging device 2.

Figure 8:
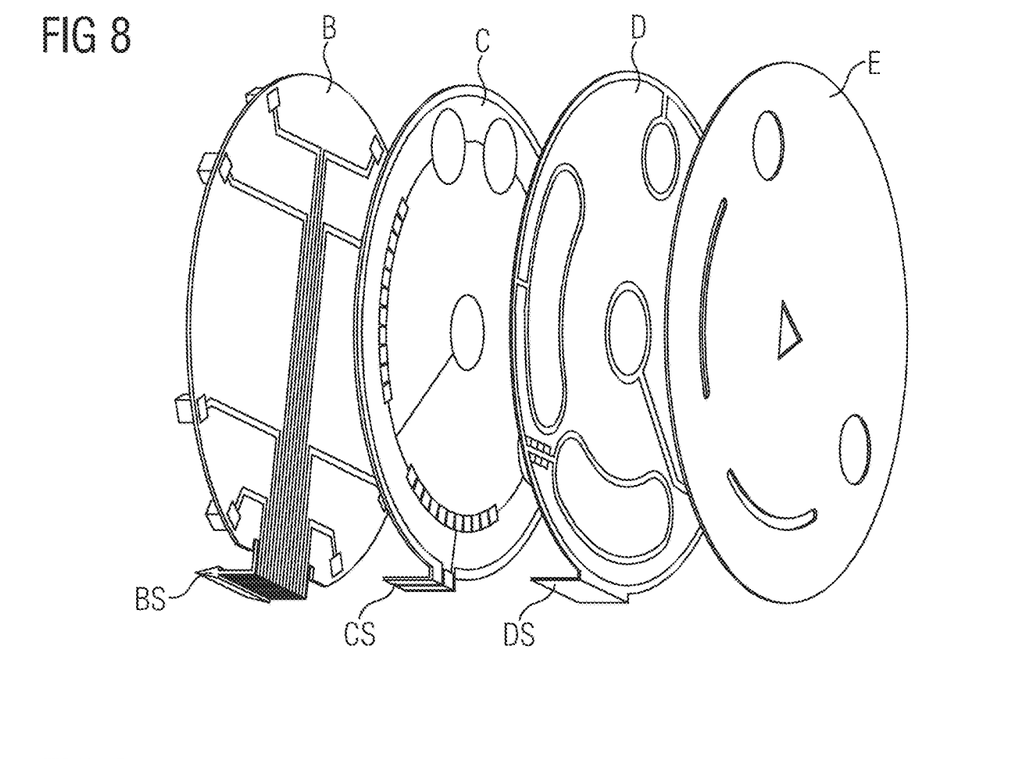
FIG. 8 shows a layered arrangement of subunits of the apparatus for operating the medical imaging device according to embodiments of the present invention.

FIG. 8 shows a layered arrangement of subunits of the apparatus 1 for operating the medical imaging device 2.

The apparatus 1 has the electronics carrier unit B of the vibration unit M, the illumination unit C, the sensor unit D and the cover layer E.

Figure 9:
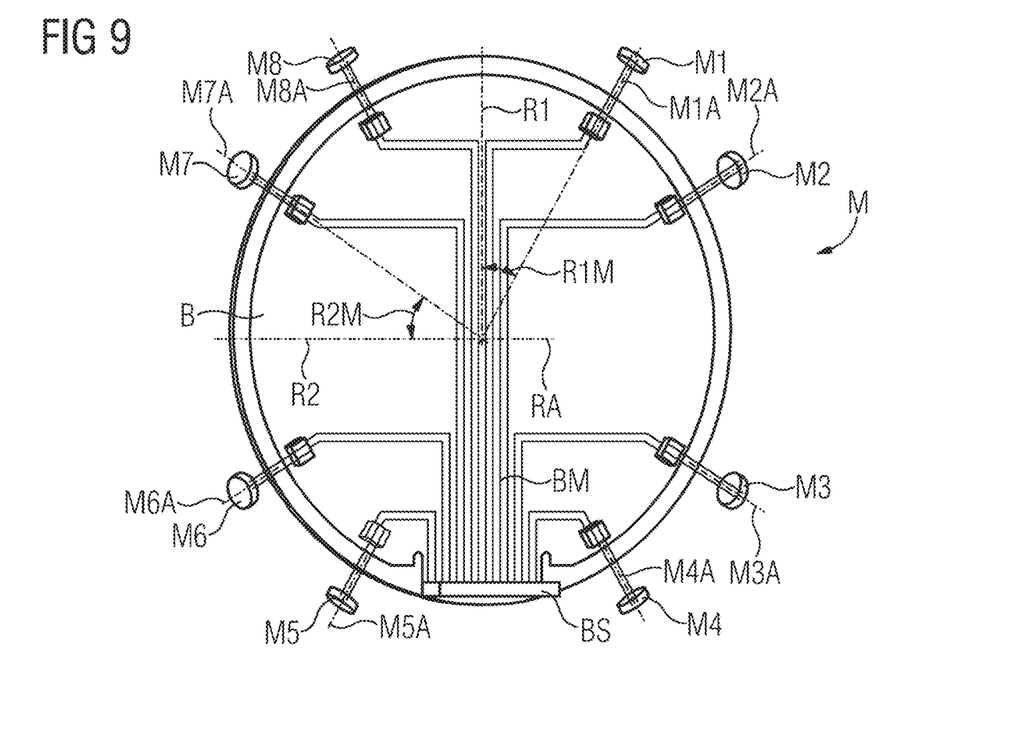
FIG. 9 shows a vibration unit with a set of vibration motors according to embodiments of the present invention.

FIG. 9 shows the vibration unit M with a set of vibration motors M1, M2, M3, M4, M5, M6, M7 and M8. The vibration motors in the set of vibration motors M1-M8 are arranged relative to one another, such that a reference plane RE runs through each vibration motor in the set of vibration motors M1-M8, wherein the vibration motors in the set of vibration motors M1-M8 are arranged around a reference axis RA perpendicular to the reference plane RE, such that the set of vibration motors M1-M8 has a corresponding vibration motor for any half-line R1, R2 which emanates from the reference axis RA and lies in the reference plane RE, so that an angular distance R1M, R2M in relation to the reference axis RA between these half-lines R1, R2 and the corresponding vibration motor, in particular between these half-lines R1, R2 and the motor axis of the corresponding vibration motor, is not greater than 45 degrees.

Each of the motor axes M1A, M2A, M3A, M4A, M5A, M6A, M7A and M8A lies in the reference plane RE and is perpendicular to the reference axis RA. The vibration unit M further has the electronics carrier unit B with electrical cables BM for controlling the vibration motors in the set of vibration motors M1-M8. The electronics carrier unit B has an interface BS for a data transfer connection to the data processing unit P.

Figure 10:
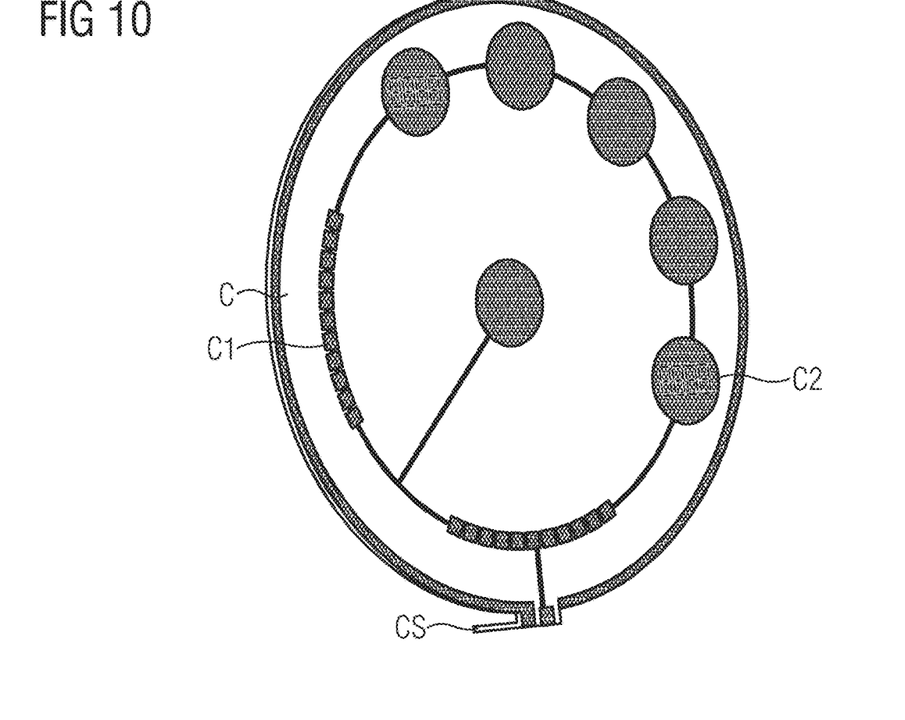
FIG. 10 shows an illumination unit according to embodiments of the present invention.

FIG. 10 shows the illumination unit C. The illumination unit C is designed to induce an illumination of the contact region N1 during contact with the contact region, in particular such that the illumination comprises visual feedback in respect of contact with the contact region, in particular comprises it in such a way. The visual feedback can in particular relate to the value for the operation of the medical imaging device. The illumination unit C can for example have an electroluminescence film for inducing the illumination.

The illumination unit C has an illuminated scale C1 in the region of the contact region N1. The illumination unit C has a display C2 in the region of the display element N2. The illumination unit C has an interface CS for a data transfer connection to the data processing unit P.

Figure 11:
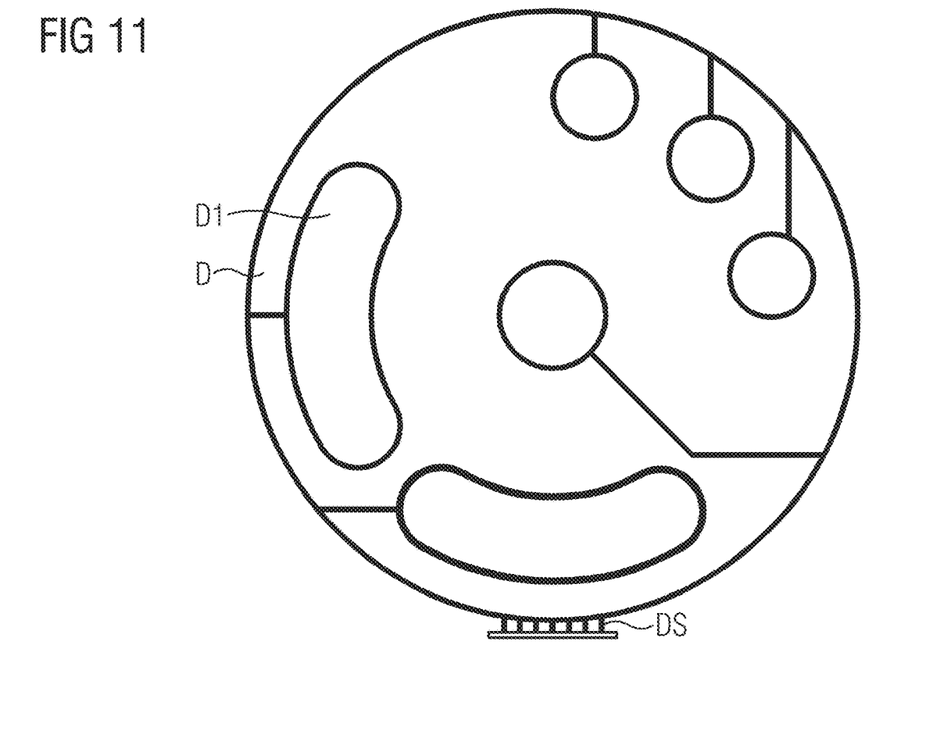
FIG. 11 shows a sensor unit according to embodiments of the present invention.

FIG. 11 shows the sensor unit D. The sensor unit D has the capacitive sensor element D1 for generating the contact signal on the basis of contact with the contact region N1. The sensor unit D has an interface DS for a data transfer connection to the data processing unit P.

Figure 12:
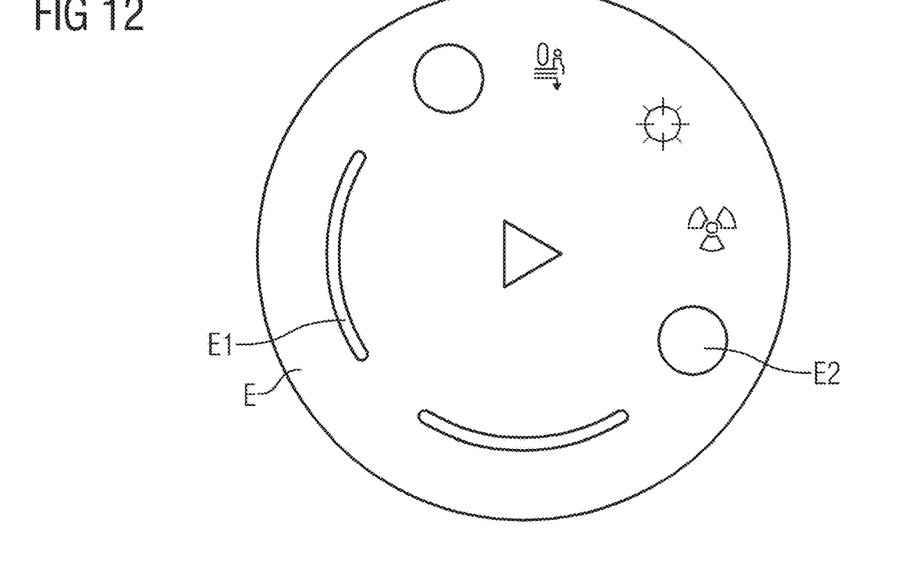
FIG. 12 shows a cover layer according to embodiments of the present invention.

FIG. 12 shows the cover layer E. The cover layer E has a cover film with the opening E1 for the visual delimitation of the illuminated scale C1 below and the opening E2 for the visual delimitation of the display C2 below. The cover layer E has further openings in the form of symbols for further control elements and/or display elements.

Figure 13:
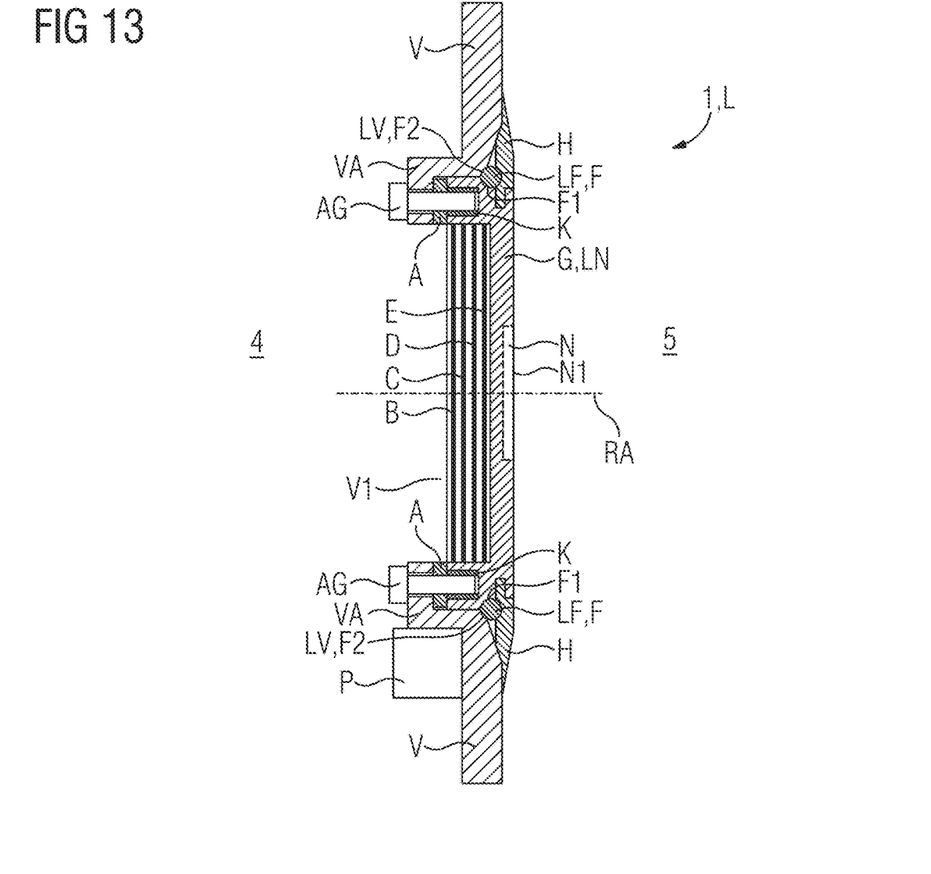
FIG. 13 shows a sectional representation through the apparatus for operating the medical imaging device according to embodiments of the present invention.

FIG. 13 shows a sectional representation of the apparatus 1 for operating the medical imaging device 2.

The connection unit L further has the housing G, the thread inserts K and the end ring H. The housing G forms the control-element-side region LN. The screws AG are inserted through holes in the connection region VA of the casing and through holes in the mounting ring A and are screwed to the thread inserts K. The thread inserts K can for example be bonded and/or fused to the housing G.

The end ring H has a sealing lip which is attached to the casing V, in particular is attached to the casing in a form-fit manner and in a manner that is impervious to liquids. The contact surface of the end ring H, which is attached to the casing V, can for example form at least one subregion of the edge region LV alternatively or additionally to F2. An annular subregion of the end ring H can in particular form at least one subregion of the flexible region LF. To this end the end ring H can be manufactured from a flexible material. The contact surface of the end ring H, which is attached to the control-element-side region LN, is fixed relative to the control-element-side region LN. The end ring H can for example be connected to the housing G via a material-bonded connection, in particular via a fused connection and/or via a multicomponent injection molding connection.

The contact surface of the mounting ring A, which is attached to the connection region VA of the casing V, can for example form at least one subregion of the edge region LV in addition to F2 and/or in addition to the contact surface of the end ring H, which is attached to the casing V. An annular subregion of the mounting ring A can in particular form at least one subregion of the flexible region LF. To this end the mounting ring A can be manufactured from a flexible material. The contact surface of the mounting ring A, which is attached to the control-element-side region LN, is fixed relative to the control-element-side region LN. The mounting ring A can for example be connected to the housing G via a material-bonded connection, in particular via a fused connection and/or via a multicomponent injection molding connection.

The edge region LV can in particular comprise a subregion of the edge region LV formed by the mounting ring A and/or a subregion of the edge region LV formed by the end ring H. The flexible region LF can in particular comprise a subregion of the flexible region LF formed by the mounting ring A and/or a subregion of the flexible region LF formed by the end ring H.

The connection unit L has a flexible sealing ring F, wherein a first annular contact surface F1 of the flexible sealing ring F is fixed relative to the control-element-side region LN, wherein a second annular contact surface F2 of the flexible sealing ring F forms at least one subregion of the edge region LV, wherein an annular subregion of the flexible sealing ring F forms at least one subregion of the flexible region LF.

The casing V has a recess V1, in which at least one part of the apparatus 1 can be accommodated, wherein the at least one part of the apparatus 1 is accommodated in the recess V1, wherein the edge region LV is attached to the casing V in a form-fit manner and in a manner that is impervious to liquids along at least one annular contour which surrounds the recess V1.

The edge region LV is fixed on the casing V relative to the casing V, in particular is fixed such that the control-element-side region LN is flexibly mounted relative to the casing via the flexible region.

Because the control-element-side region LN is mounted flexibly relative to the casing V, the oscillations of the vibration are sufficiently decoupled from the casing V in respect of damping and can thus be detected by the user.

Figure 14:
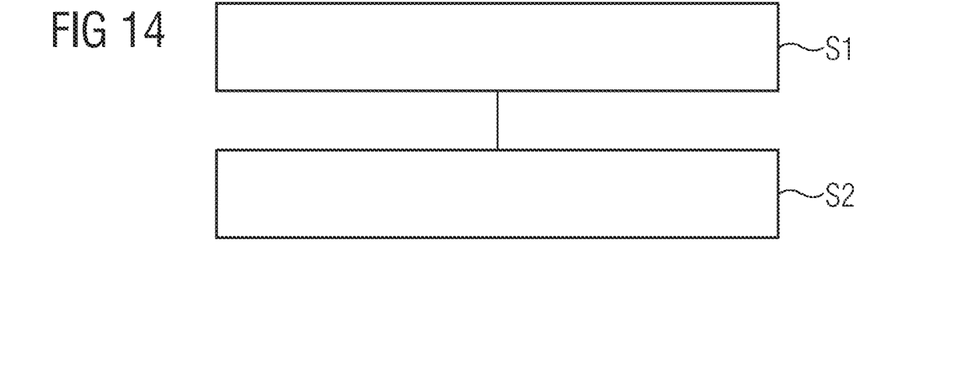
FIG. 14 shows a flow diagram for a method for operating a medical imaging device according to embodiments of the present invention.

FIG. 14 shows a flow diagram for a method for operating a medical imaging device 2 via an apparatus 1,
wherein the apparatus 1 has a control unit N, a connection unit L and a vibration unit M,
wherein the connection unit L has a control-element-side region LN, an edge region LV and a flexible region LF, wherein the control-element-side region LN is flexibly mounted relative to the edge region LV via the flexible region LF,
wherein the control unit N has a contact region N1, wherein the contact region N1 is fixed relative to the control-element-side region LN,
wherein a contact signal is generated S1 via the control unit N on the basis of contact with the contact region N1,
wherein a vibration of the contact region N1 relative to the edge region LV is induced S2 via the vibration unit M during contact with the contact region N1, in particular is induced such that the vibration comprises tactile feedback in respect of contact with the contact region N1, in particular such that the tactile feedback is detected via contact with the contact region N1.

Figure 15:
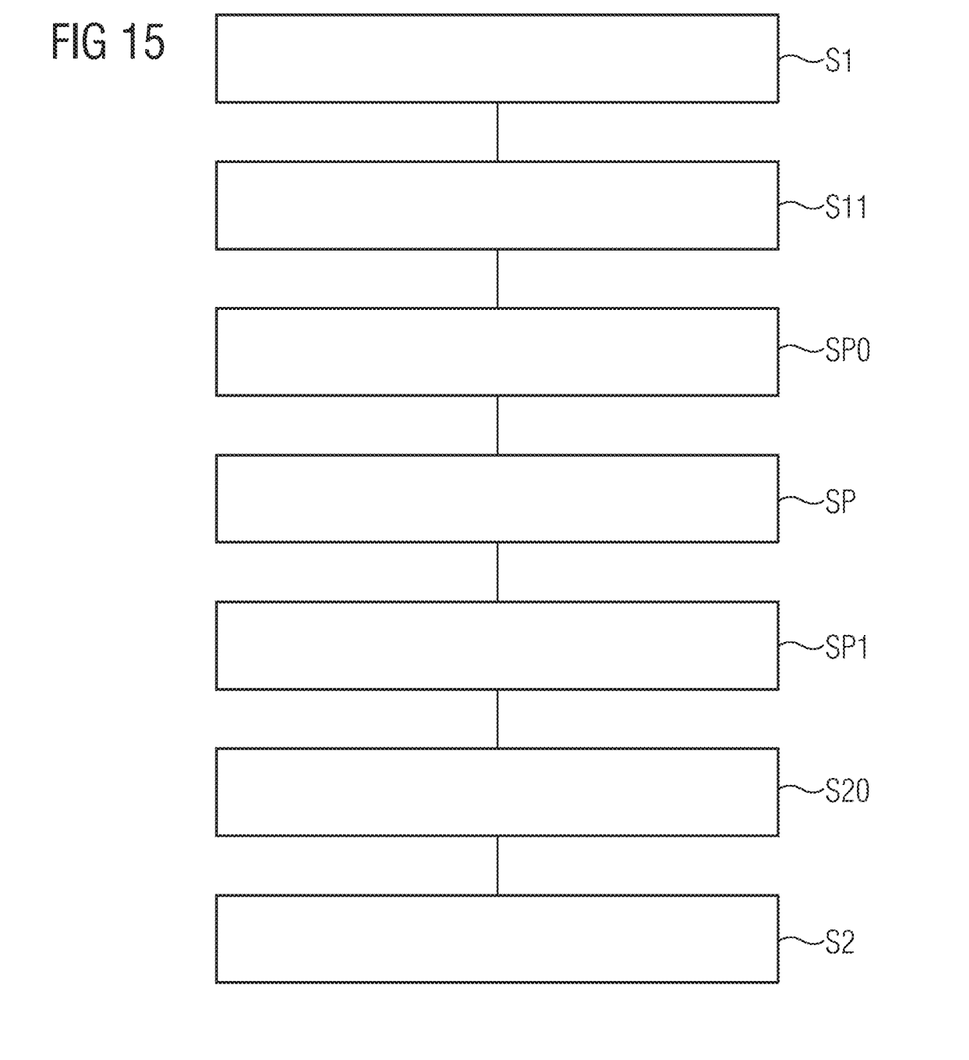
FIG. 15 shows a further example of a flow diagram for a method for operating a medical imaging device according to embodiments of the present invention.

FIG. 15 shows a further example of a flow diagram for a method for operating a medical imaging device 2,
wherein the contact signal is sent S11 to a data processing unit P via the control unit N, wherein the contact signal is received SP0 via the data processing unit P, a vibration signal is generated SP on the basis of the contact signal and the vibration signal is sent SP1 to the vibration unit M, wherein the vibration signal is received S20 via the vibration unit M and the vibration of the contact region N1 relative to the edge region LV is induced S2 on the basis of the vibration signal.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Where it has not explicitly occurred, but expedient and within the meaning of the present invention, individual example embodiments, individual partial aspects or features thereof can be combined with each other or interchanged without departing from the scope of the present invention. Advantages of the present invention described with regard to one embodiment also apply without being explicit mentioned, and where transferable, to other embodiments.

What is claimed is:

1. An apparatus for operating a medical imaging device, the apparatus comprising:
    a connection unit having a control-element-side region, an edge region and a flexible region, the control-element-side region being flexibly mounted relative to the edge region via the flexible region;
    a control unit having a contact region, the contact region being fixed relative to the control-element-side region, and the control unit being configured to generate a contact signal based on a contact with the contact region; and
    a vibration unit configured to induce a vibration of the contact region relative to the edge region during the contact with the contact region.

2. The apparatus as claimed in claim 1,
    wherein the control unit is further configured to send the contact signal to a data processing unit,
    wherein the data processing unit is configured to
        receive the contact signal,
        generate a vibration signal based on the contact signal, and
        send the vibration signal to the vibration unit, and
            wherein the vibration unit is further configured to
        receive the vibration signal, and
        induce the vibration of the contact region relative the edge region based on the vibration signal.

3. The apparatus as claimed in claim 2, further comprising the data processing unit.

4. The apparatus as claimed in claim 2,
    wherein the contact with the contact region relates to an input of a value for operation of the medical imaging device, and
    wherein the vibration of the contact region relative to the edge region during the contact with the contact region includes tactile feedback, which relates to the value for the operation of the medical imaging device.

5. The apparatus as claimed in claim 2,
    wherein the vibration unit has a set of vibration motors,
    wherein vibration motors in the set of vibration motors are arranged relative to one another, such that a reference plane runs through each vibration motor in the set of vibration motors, and
    wherein the vibration motors in the set of vibration motors are arranged about a reference axis perpendicular to the reference plane, such that the set of vibration motors has a corresponding vibration motor for any half-line emanating from the reference axis and lies in the reference plane, so that an angular distance relative to the reference axis between the half-lines and the corresponding vibration motor is not greater than 60 degrees.

6. The apparatus as claimed in claim 2,
    wherein the connection unit has a flexible sealing ring,
    wherein a first annular contact surface of the flexible sealing ring is fixed relative to the control-element-side region,
    wherein a second annular contact surface of the flexible sealing ring forms at least one subregion of the edge region, and
    wherein an annular subregion of the flexible sealing ring forms at least one subregion of the flexible region.

7. The apparatus as claimed in claim 1,
    wherein the contact with the contact region relates to an input of a value for operation of the medical imaging device, and
    wherein the vibration of the contact region relative to the edge region during the contact with the contact region includes tactile feedback, which relates to the value for the operation of the medical imaging device.

8. The apparatus as claimed in claim 7,
wherein the vibration of the contact region relative to the edge region during the contact with the contact region forms a carrier signal, and
wherein the carrier signal is modulated with a useful signal, which relates to the value for the operation of the medical imaging device.

9. The apparatus as claimed in claim 8, wherein a parameter of the vibration is a monotonic function of the value for the operation of the medical imaging device.

10. The apparatus as claimed in claim 7, wherein a parameter of the vibration is a monotonic function of the value for the operation of the medical imaging device.

11. The apparatus as claimed in claim 1,
wherein the vibration unit has a set of vibration motors,
wherein vibration motors in the set of vibration motors are arranged relative to one another, such that a reference plane runs through each vibration motor in the set of vibration motors, and
wherein the vibration motors in the set of vibration motors are arranged about a reference axis perpendicular to the reference plane, such that the set of vibration motors has a corresponding vibration motor for any half-line emanating from the reference axis and lies in the reference plane, so that an angular distance relative to the reference axis between the half-lines and the corresponding vibration motor is not greater than 60 degrees.

12. The apparatus as claimed in claim 1,
wherein the connection unit has a flexible sealing ring,
wherein a first annular contact surface of the flexible sealing ring is fixed relative to the control-element-side region,
wherein a second annular contact surface of the flexible sealing ring forms at least one subregion of the edge region, and
wherein an annular subregion of the flexible sealing ring forms at least one subregion of the flexible region.

13. A medical imaging device, comprising:
the apparatus as claimed in claim 1; and
a casing configured to delimit an internal region of the medical imaging device from a surrounding area, wherein
the surrounding area surrounds the medical imaging device, and
the edge region is fixed on the casing relative to the casing.

14. The medical imaging device as claimed in claim 13,
wherein the casing has a recess configured to accommodate at least a part of the apparatus,
wherein the at least a part of the apparatus is accommodated in the recess, and
wherein the edge region is attached to the casing in a form-fit manner and in a manner that is impervious to liquids along at least one annular contour that surrounds the recess.

15. A method for operating a medical imaging device via an apparatus, the apparatus having a control unit, a connection unit and a vibration unit, wherein the connection unit has a control-element-side region, an edge region and a flexible region, the control-element-side region being flexibly mounted relative to the edge region via the flexible region, wherein the control unit has a contact region, the contact region being fixed relative to the control-element-side region, the method comprising:
generating, by the control unit, a contact signal based on a contact with the contact region; and
inducing, by the vibration unit, a vibration of the contact region relative to the edge region during the contact with the contact region.

16. The method as claimed in claim 15, further comprising:
sending, by the control unit, the contact signal to a data processing unit,
receiving the contact signal at the data processing unit,
generating a vibration signal based on the contact signal,
sending the vibration signal to the vibration unit,
receiving the vibration signal at the vibration unit, and
inducing the vibration of the contact region relative to the edge region based on the vibration signal.

17. The method as claimed in claim 16,
wherein the contact with the contact region relates to an input of a value for operation of the medical imaging device, and
wherein the vibration of the contact region relative to the edge region during the contact with the contact region includes tactile feedback, which relates to the value for the operation of the medical imaging device.

18. The method as claimed in claim 15,
wherein the contact with the contact region relates to an input of a value for operation of the medical imaging device, and
wherein the vibration of the contact region relative to the edge region during the contact with the contact region includes tactile feedback, which relates to the value for the operation of the medical imaging device.

19. The method as claimed in claim 18,
forming a carrier signal via the vibration of the contact region relative to the edge region during the contact with the contact region, and
modulating the carrier signal with a useful signal, which relates to the value for the operation of the medical imaging device.

20. The method as claimed in claim 18, wherein a parameter of the vibration is a monotonic function of the value for operation of the medical imaging device.

* * * * *